(12) United States Patent
Yang et al.

(10) Patent No.: US 8,052,997 B2
(45) Date of Patent: Nov. 8, 2011

(54) ANTI-BACTERIAL COMPOSITION AND METHOD FOR PRODUCING THE SAME

(75) Inventors: Cheng-Chien Yang, Longtan Township, Taoyuan County (TW); Kuo-Hui Wu, Taoyuan (TW); Wang-Tsai Gu, Longtan Township, Taoyuan County (TW); Chin-Yih Chen, Longtan Township, Taoyuan County (TW); Fu-Chu Yang, Taoyuan (TW)

(73) Assignee: Chung-Shan Institute of Science and Technology Armaments Bureau, Ministry of National Defense, Taoyuan County (TW)

( * ) Notice: Subject to any disclaimer, the term of this patent is extended or adjusted under 35 U.S.C. 154(b) by 371 days.

(21) Appl. No.: 12/426,195

(22) Filed: Apr. 17, 2009

(65) Prior Publication Data

US 2010/0266688 A1   Oct. 21, 2010

(51) Int. Cl.
  *A61K 9/14* (2006.01)
  *A61K 33/38* (2006.01)
(52) U.S. Cl. .................................. 424/484; 424/618
(58) Field of Classification Search .................. None
  See application file for complete search history.

(56) References Cited

U.S. PATENT DOCUMENTS

2009/0175948 A1*   7/2009   Jiang et al. .................... 424/490
* cited by examiner

*Primary Examiner* — Janet L Epps-Smith

(57) ABSTRACT

The invention discloses an anti-bacterial composition and method for producing the same. The anti-bacterial composition of the invention includes an organic siloxane material which comprises an amino group, and a plurality of silver atoms. Particularly, the organic siloxane material has a meshed structure, and the plurality of silver atoms are bonded to the amino group and are well dispersed in the meshed structure.

4 Claims, 9 Drawing Sheets

ANTI-BACTERIAL COMPOSITION AND METHOD FOR PRODUCING THE SAME

BACKGROUND OF THE INVENTION

1. Field of the Invention

The present invention relates to an anti-bacterial composition and method for producing the same, and more particularly, to an anti-bacterial composition comprising silver atoms and method for producing the same.

2. Description of the Prior Art

There are many different anti-bacterial agents, and the purpose of most of them is not to eliminate harmful microorganism immediately, but to suppress the growth and the reproduction of the harmful microorganism for long-term using process to achieve the purpose of protecting human body's health. The anti-bacterial agents can be divided into inorganic type, organic type and natural type. The inorganic type anti-bacterial agents may also be divided into metallic ion type, photocatalysis type and complex type.

In addition, the metallic ion type anti-bacterial agents are formed by physical absorption or ion exchange to make the metal such as silver, copper, zinc and so on to be fixed on the surface of zeolite, silica gel or other suitable porous material. The metallic ion type anti-bacterial agents utilize the anti-bacterial ability of the metal to suppress the growth of the harmful microorganism. Moreover, the metallic ion type anti-bacterial agents have great application and can be mixed with different polymers to form fiber, plastic, paint and so on by different processing methods. However, because the properties of the interfaces of the metallic ions and the polymer are quite different, the metallic ions are easy to accumulate and not easy to be dispersed well in the polymer.

SUMMARY OF THE INVENTION

Accordingly, an aspect of the present invention is to provide an anti-bacterial composition comprising silver atoms, wherein the silver atoms are well dispersed in the polymer.

According to an embodiment, the anti-bacterial composition of the invention comprises an organic siloxane material which has an amino group and a plurality of silver atoms. Particularly, the organic siloxane material has a meshed structure, and the plurality of silver atoms are well dispersed in the meshed structure by binding to the amino group.

Another aspect of the present invention is to provide a method of manufacturing said anti-bacterial composition.

According to an embodiment, the method of the invention comprises the steps of: (a) mixing tetraethyl orthosilicate with aminosilane, stirring the mixture in nitrogen to form an organic siloxane material comprising an amino group, and the organic siloxane material having a meshed structure; (b) dissolving silver salts in ammonium hydroxide and adding the dissolved silver salts into the organic siloxane material to dissociate silver ions from the silver salts; and (c) adding hydrazine into the mixture of step (b), stirring the mixture in nitrogen to reduce the silver ions to form silver atoms, so that the silver atoms are well dispersed in the meshed structure of the organic siloxane material to obtain the anti-bacterial composition.

The objective of the present invention will no doubt become obvious to those of ordinary skill in the art after reading the following detailed description of the preferred embodiment, which is illustrated in following figures and drawings.

BRIEF DESCRIPTION OF THE APPENDED DRAWINGS

DETAILED DESCRIPTION OF THE INVENTION

The invention provides an anti-bacterial composition comprising silver atoms and method for producing the anti-bacterial composition. The detail of the method is well described in the following specification, and physical and chemical characteristics of the anti-bacterial composition are tested.

Embodiment 1

Specimen Preparation

Firstly, a diamond cutter is used to cut an aluminum alloy specimen to two different size of 2.5 cm×5 cm×1 mm and 5 cm×5 cm×1 mm. After that, a polisher is used to polish the surface of the aluminum alloy specimen. Then, acetone is used to de-esterify the surface of the specimen. Afterward, the aluminum alloy specimen implements a minute immersion and clean under 5% NaOH at 50° C. temperature (soda wash), and then implements 30 seconds immersion and clean under 1:1 HNO$_3$ aqueous solution (acid pickling). Finally, after clean it by clear water, and then dry it, the specimen is finished.

Embodiment 2

Manufacturing Anti-Bacterial Composition of the Invention

In this embodiment, the anti-bacterial composition of the invention manufactures according to the steps of: firstly, tetraethyl orthosilicate (TEOS, $C_8H_{20}O_4Si$) and aminosilane are used as raw materials, which are dissolved in 60 ml deionized water at molar ratio of 1:1, and are stirred evenly under nitrogen for 48 hours.

In practice, the aminosilane can be chosen as 3-(2-aminoethylaminopropyl)trimethoxysilane (AES, $(CH_3O)_3Si(CH_2)_3 NHCH_2CH_2NH_2$)) (purity $\geqq 80\%$, produced by American Aldrich Corporation) or N-[3-(trimethoxysilyl)propyl]diethylenetriamine (ATS, $(CH_3O)_3Si(CH_2)_3(NHCH_2CH_2)_2NH_2$)) (97% purity, produced by American Aldrich Corporation).

Afterward, silver nitrate ($AgNO_3$) (99% purity, produced by German Merck Corporation) is dissolved in ammonium hydroxide ($NH_4OH$) (content 28%, produced by Japanese Reagent Industry Joint-stock Corporation), and then said mixed solution is added.

Figure 1:
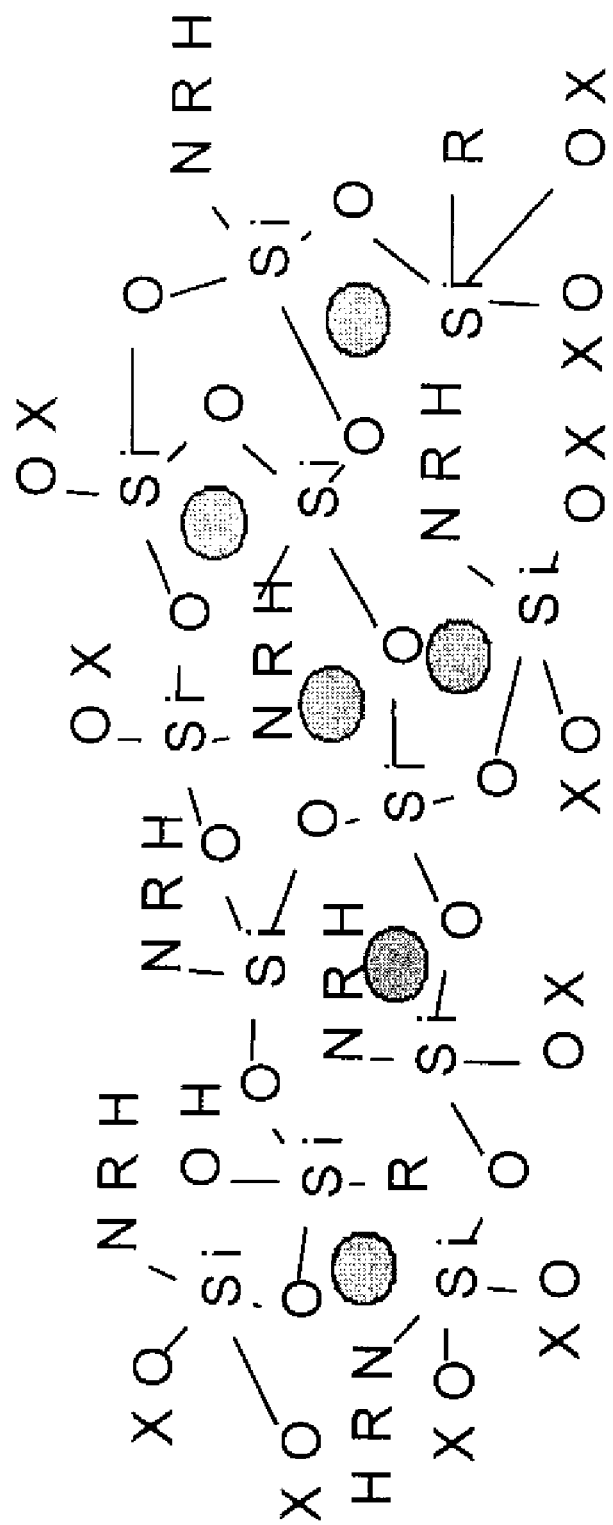
FIG. 1 is a chemical structure diagram illustrating an anti-bacterial composition according to an embodiment of the invention.

Then, hydrazine ($N_2H_4$) (99% purity, produced by Japan Shouwa Chemistry Joint-stock Corporation) is added into said mixed solution and stirred evenly under nitrogen for 12 hours. After filtering, washing, and drying processes, the anti-bacterial composition of the invention Ormosil(ATS)/Ag or Ormosil(AES)/Ag is obtained. Please refer to FIG. 1. FIG. 1 is a chemical structure diagram illustrating the anti-bacterial composition according to the embodiment of the invention, wherein the black solid circles in FIG. 1 is silver.

In the embodiment, three kinds of anti-bacterial compositions are prepared respectively with the reaction of (TEOS+ATS) and $AgNO_3$ in different weight ratios of 1:0.1, 1:0.05 and 1:0.025, and are abbreviated as Ormosil(ATS)/Ag-0.1, Ormosil(ATS)/Ag-0.05 and Ormosil(ATS)/Ag-0.025.

Additionally, three kinds of anti-bacterial compositions are also prepared respectively with the reaction of (TEOS+AES) and $AgNO_3$ in different weight ratios of 1:0.1, 1:0.05 and 1:0.025, and are abbreviated as Ormosil(AES)/Ag-0.1, Ormosil(AES)/Ag-0.05 and Ormosil(AES)/Ag-0.025.

In addition, said anti-bacterial compositions can be coated on said specimen for the convenience of future examination. For example, a spin coater is used to coat three layers of gelable mixed liquor on the 2024-T3 aluminum alloy of 2.5 cm×5 cm×1 mm. Then, the coated aluminum alloy and remaining solution are dried for two hours respectively at room temperature, 60° C. and 120° C. After drying, the specimen is used to do salt-spray test and electrochemical test, while the remaining powder is used to do spectrum analysis.

Embodiment 3

Fourier-Transform Infrared Spectrometer Analysis

The characteristic of compound structure can be analyzed by using Fourier-Transform Infrared Spectrometer (FT-IR) (TENSOR27, scanned range: 400~4000 $cm^{-1}$) and BRUKER DSX 400 MHz Solid State NMR of $^{13}C$ and $^{29}Si$. Because $(RSiO_{3/2})_n$ of $T^i$ structure and $(SiO_2)_m$ of $Q^i$ structure in the compound have different electronic environments, we may use solid state $^{13}C$ and $^{29}Si$ NMR cross-polarization method to analyze the condensation degree of tetraethyl orthosilicate and aminosilane and the influence of metal silver to its structure.

Figure 2A:
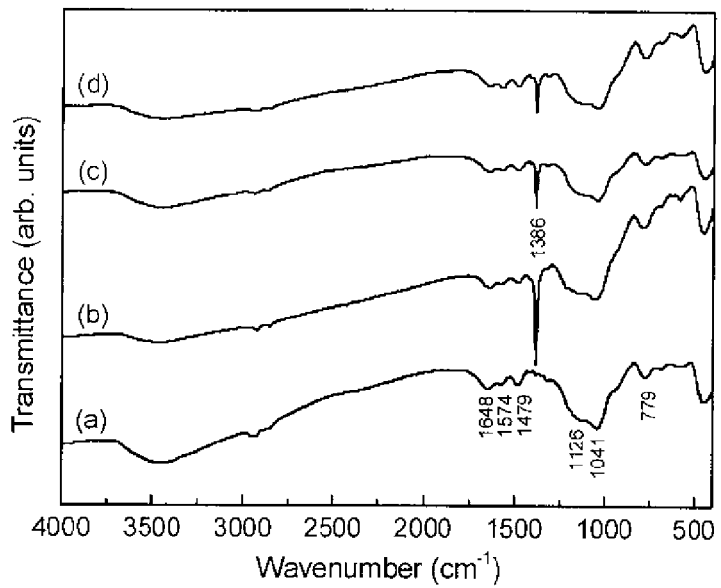
FIG. 2A is an infrared spectrum diagram illustrating Ormosil(ATS)/Ag complexes with different silver content.
Figure 2B:
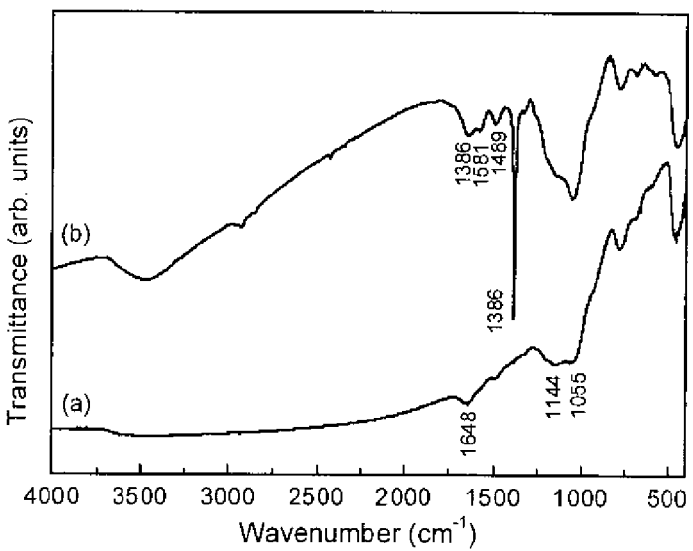
FIG. 2B is an infrared spectrum diagram illustrating Ormosil(ATS)/Ag complexes with different silver content.

Please refer to FIG. 2A, which is an infrared spectrum diagram illustrating Ormosil(ATS)/Ag complexes with different silver content, wherein (a) is the spectrum of Ormosil (ATS), (b) is the spectrum of Ormosil(ATS)/Ag-0.1, (c) is the spectrum of Ormosil(ATS)/Ag-0.05 and (d) is the spectrum of Ormosil(ATS)/Ag-0.025. 1126, 779 and 460 are three characteristic absorption peaks of $SiO_2$ in the figure and correspond respectively to unsymmetrical stretching, symmetrically stretching and bending vibration absorption of Si—O—Si. 3460, 2936, 2867, 1648, 1574, 1479 and 1041 $cm^{-1}$ are characteristic absorption peaks of Ormosil. 3460 $cm^{-1}$ is vibration absorption peak of O—H or N—H. 2936 and 2867 $cm^{-1}$ are symmetrical and unsymmetrical stretching vibration of different types C—H. 1648, 1574, 1479 and 1041 $cm^{-1}$ are bending vibration absorption of C—C, C—H, N—H, C—N. 1386 $cm^{-1}$ is vibration absorption of $NO_3^-$ ion. When the proportion of $AgNO_3$ increases, the intensity of the vibration absorption of $NO_3^-$ ion also increases. Additionally, the intensity of the vibration absorption peak (3460 $cm^{-1}$) of N—H is getting weak along with the increase of the proportion of $AgNO_3$, but the characteristic absorption peak of $SiO_2$ keeps invariable. It means that there is an interaction between Ag and the amino group of Ormosil. FIG. 2B is an infrared spectrum diagram illustrating Ormosil(AES) and Ormosil (AES)/Ag-0.05 complexes.

Embodiment 4

X-Ray Diffractometer Analysis

In the embodiment, X-Ray Diffractometer (XRD) is used to carry on analysis for the anti-bacterial composition of the invention. The used XRD here is SIEMENS D5000& ENRAF-NONIUS, 852DX60D, wherein voltage is 40 kV, current is 30 mA, light source is Cu—Kα target, scanned rate is 1.5°/min, and scanned range is 20~80°.

Figure 3A:
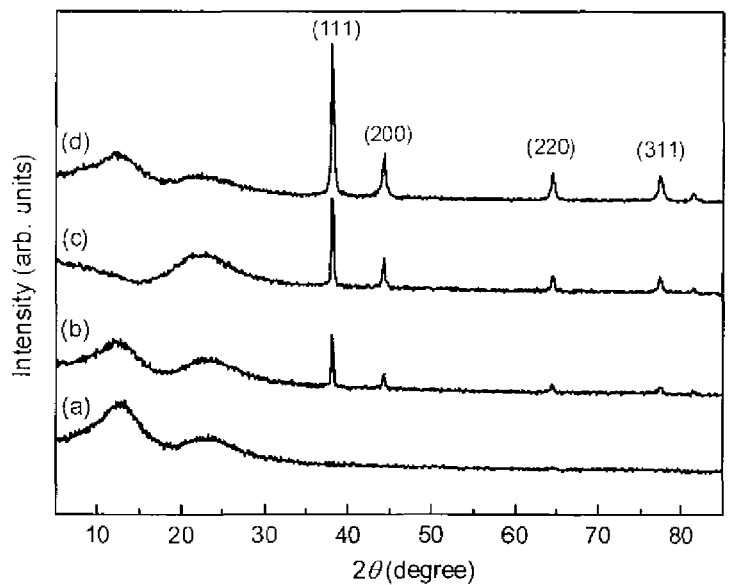
FIG. 3A is an X-ray diffraction pattern illustrating Ormosil(ATS)/Ag complexes with different silver content.

Please refer to FIG. 3A, which is an X-ray diffraction pattern illustrating Ormosil(ATS)/Ag complexes with different silver content, wherein (a) is the spectrum of Ormosil (ATS), (b) is the spectrum of Ormosil(ATS)/Ag-0.025, (c) is the spectrum of Ormosil(ATS)/Ag-0.05 and (d) is the spectrum of Ormosil(ATS)/Ag-0.1.

Compared to JCPDS data base, it can be proved that amorphous phase $SiO_2$ and polycrystalline phase metal silver are included in the complex. Moreover, the intensity of the complex increases along with the increase of the proportion of $AgNO_3$. The regions of 2θ=12° and 20-25° in the figure are non-stereotyping Ormosil meshed structure. In addition, the regions of 2θ=38°, 44°, 65°, 78° are characteristic absorption peaks of Ag (111), (200), (220), (311). Scherrer formula $D=0.9\lambda/\beta \cos\theta$ is used to calculate (111) diffraction peak of XRD atlas, wherein D is grain size (nm), λ is radiation wavelength (Cu $K_\alpha$ is 0.154056 nm), β is half width at half maximum (HWHM) of the diffraction peak, and θ is angle of the diffraction peak. It is obtained that the average grain diameter of Ag is approximately 10-30 nm. It is demonstrated that the Ag dispersed in the meshed structure of Ormosil is nano-scale grain.

Figure 3B:
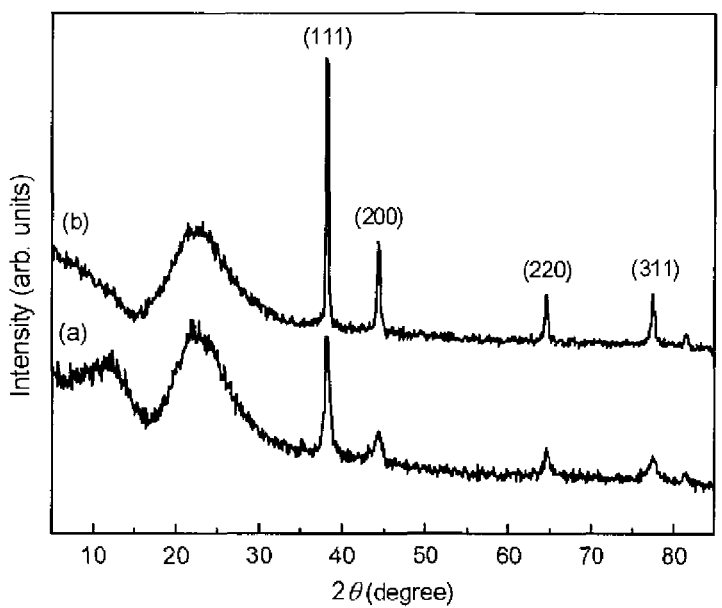
FIG. 3B is an X-ray diffraction pattern illustrating Ormosil(AES)/Ag-0.05 complex (a) and Ormosil(ATS)/Ag-0.05 complex (b) with equal silver content.

Please refer to FIG. 3B, which is an X-ray diffraction pattern illustrating Ormosil(AES)/Ag-0.05 complex (a) and Ormosil(ATS)/Ag-0.05 complex (b) with equal silver content. As shown in FIG. 3B, the intensity of Ormosil(ATS)/Ag-0.05 is stronger than that of Ormosil(AES)/Ag-0.05 according to the characteristic absorption peaks of metal silver. It means that the content of Ag absorbed by Ormosil(ATS)/Ag is higher than Ormosil(AES)/Ag. The possible reason is that Ormosil(ATS) comprises more amino group than Ormosil (AES).

Embodiment 5

$^{13}C$-, $^{29}Si$-NMR Spectrum Analysis

Figure 4A:
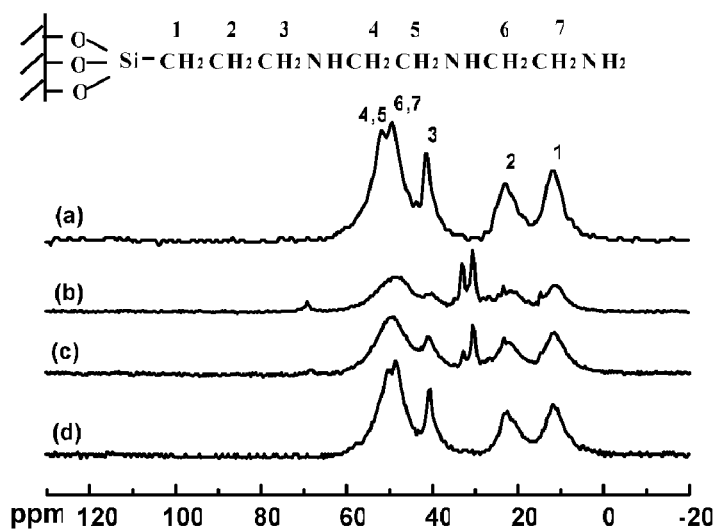
FIG. 4A is a $^{13}$C-NMR spectrum diagram illustrating Ormosil(ATS)/Ag complexes with different silver content.

Please refer to FIG. 4A, which is a $^{13}C$-NMR spectrum diagram illustrating Ormosil(ATS)/Ag complexes with different silver content, wherein (a) is Ormosil(ATS), (b) is Ormosil(ATS)/Ag-0.1, (c) is Ormosil(ATS)/Ag-0.05 and (d) is Ormosil(ATS)/Ag-0.025. By using $^{13}$C CP/MAS NMR spectrum to analyze the organic segment structure of Ormosil (ATS), we can find that Ormosil(ATS) is consisted of: 11.7 ppm [Si—CH$_2$CH$_2$], 22.9 ppm [Si—CH$_2$CH$_2$CH$_2$], 41.4 ppm [Si—CH$_2$CH$_2$CH$_2$NH], 49.3 ppm [Si—CH$_2$CH$_2$CH$_2$NHCH$_2$CH$_2$NHCH$_2$NH$_2$] and 51.8 ppm [Si—CH$_2$CH$_2$CH$_2$NHCH$_2$CH$_2$NHCH$_2$CH$_2$NH$_2$]. Ormosil(ATS)/Ag complex appears a new absorption peak between 30-33 ppm and the intensity of the whole absorption peak becomes weaker obviously. It's mainly because the silver is absorbed at the position of the amino groups. It makes the overlap carbon nucleus absorption near the amino groups presents fission and partial carbon nucleus energy is dispersed to the d-orbital of the silver simultaneously. However, Ormosil (ATS)/Ag-0.025 complex has no such phenomenon. It is possible because the silver content is too low.

Figure 4B:
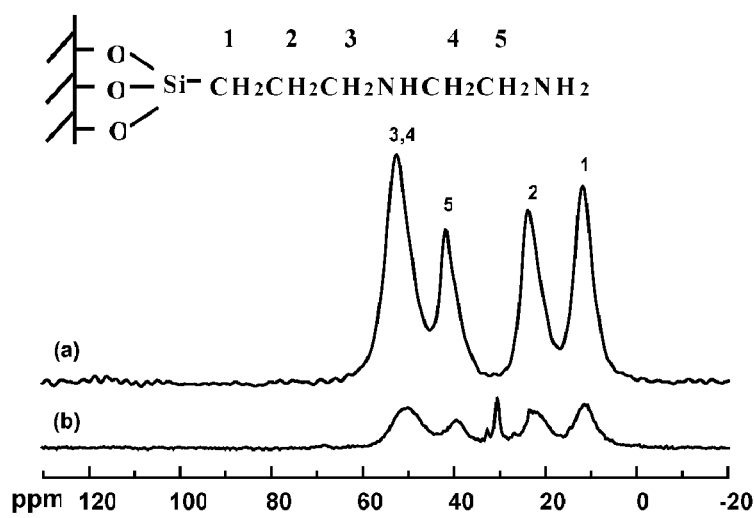
FIG. 4B is a $^{13}$C-NMR spectrum diagram illustrating Ormosil(AES)/Ag complexes with different silver content.

Please refer to FIG. 4B, which is a $^{13}$C-NMR spectrum diagram illustrating Ormosil(AES)/Ag complexes with different silver content, wherein (a) is Ormosil(AES) and (b) is Ormosil(AES)/Ag-0.05. By using $^{13}$C CP/MAS NMR spectrum to analyze the organic segment structure of Ormosil (AES), we can find that Ormosil(AES) is consisted of: 11.8 ppm [Si—CH$_2$CH$_2$], 23.8 ppm [Si—CH$_2$CH$_2$CH$_2$], 41.7 ppm [Si—CH$_2$CH$_2$CH$_2$NHCH$_2$CH$_2$NH$_2$] and 52.6 ppm [Si—CH$_2$CH$_2$CH$_2$NHCH$_2$CH$_2$NH$_2$]. Ormosil(AES)/Ag complex appears a new absorption peak at 30.5 ppm, which is formed mainly because the Ag is absorbed at the position of the amino groups, such that the electron environment of two C atoms near the amino group has changed. In addition, the intensity of the NMR absorption peak of Ormosil(AES)/Ag complex becomes weaker. At the same time, the position of the absorption peak of the C around the amino group shifts to right (52.6→50.1 ppm; 41.7→39.4 ppm). All these results can approve that the Ag is absorbed around the amino group of Ormosil.

Figure 5A:
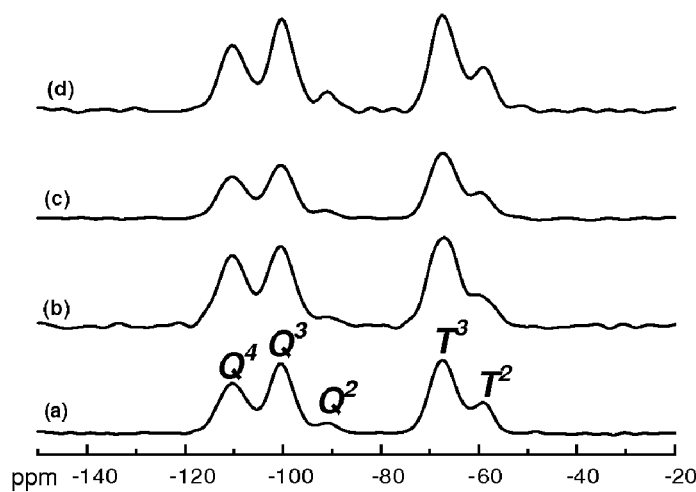
FIG. 5A is a $^{29}$Si-NMR spectrum diagram illustrating Ormosil(ATS)/Ag complexes with different silver content.

Please refer to FIG. 5A, which is a $^{29}$Si-NMR spectrum diagram illustrating Ormosil(ATS)/Ag complexes with different silver content, wherein (a) is Ormosil(ATS), (b) is Ormosil(ATS)/Ag-0.1, (c) is Ormosil(ATS)/Ag-0.05 and (d) is Ormosil(ATS)/Ag-0.025.

By using the $^{29}$Si CP/MAS NMR spectrum to analyze the organic segment structure of Ormosil(ATS), we can find that Ormosil(ATS) is consisted of: −59.0 ppm [T$^2$; R—Si(OSi)$_2$(OH)], −67.4 ppm [T$^3$; R—Si(OSi)$_3$], −90.9 ppm [Q$^2$; Si(OSi)$_2$(OH)$_2$], −100.4 ppm [Q$^3$; Si(OSi)$_3$(OH)] and −110.3 ppm [Q$^4$; Si(OSi)$_4$], wherein T$^3$ and Q$^3$ are main structures. The $^{29}$Si-NMR spectrum of Ormosil(ATS)/Ag complex is similar to the one of Ormosil(ATS). It means that the Ag absorbed around the amino group of Ormosil has no obvious influence on the inorganic segment (SiO$_2$) structure of Ormosil.

In cross-polarization procedure, the spin of rotating coordinates system $^1$H and $^{13}$C lock it and carry on thermo-contact each other, hereby energy is exchanged mutually, and individual spin system also carries on energy exchange with environment (crystal lattice) around. The $T^H_{1\rho}$ value can be obtained base on the relationship between the magnetic susceptibility $M_c(t)$ of $^{13}$C and the contact time t.

Figure 5B:
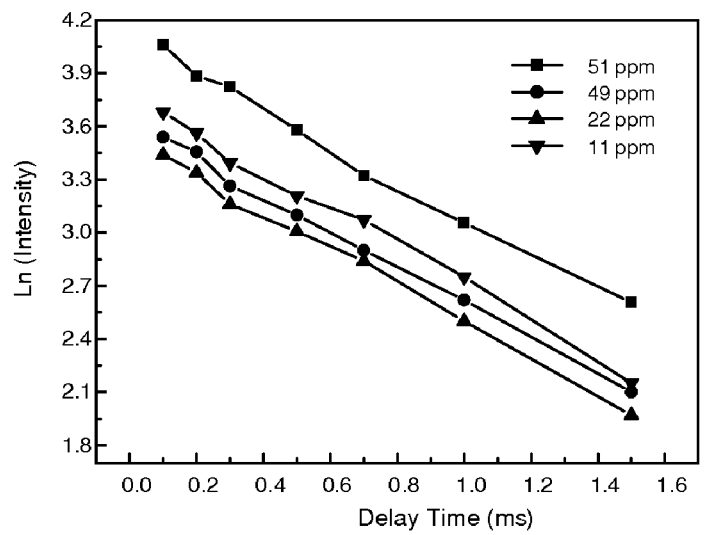
FIG. 5B and FIG. 5C are relationship diagrams of semi-log of carbon wave peak intensity and contact time respectively illustrating Ormosil(ATS)/Ag and Ormosil(ATS)/Ag-0.05.
Figure 5C:
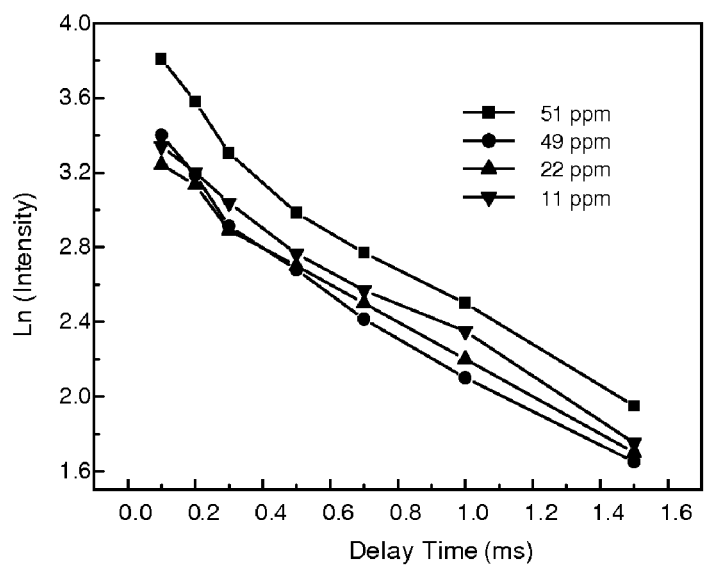

Please refer to FIG. 5B and FIG. 5C, which are relationship diagrams of semi-log of carbon wave peak intensity and contact time respectively illustrating Ormosil(ATS)/Ag and Ormosil(ATS)/Ag-0.05. The steeper the slope, the faster the spin diffuses to relax (the shorter the $T^H_{1\rho}$). Different relaxation behavior can be used to discuss the mobility of aminosilane organic segment. Compared $T^H_{1\rho}$ (please refer to the following Table 1) calculated from the slopes of FIG. 5B and FIG. 5C to the data of the salt-spray test, it can be verified the influence of the segment mobility and the microstructure on the corrosion resistance. Base on the analysis of $^1$H spin-crystal lattice relaxation time $T^H_{1\rho}$ on the mobility of the organic segment of the complex, it can be found that the $T^H_{1\rho}$ value of Ormosil(ATS)/Ag-0.05 is smaller than the one of Ormosil(ATS). The $T^H_{1\rho}$ value becoming smaller means that $^1$H spin-diffusion is very fast, i.e. the added metal silver makes the complex structure to be closer and harder.

TABLE 1

| SAMPLE | $T_{1\rho}^H$ (ms); amine unit | | | | |
|---|---|---|---|---|---|
| | 11 ppm | 22 ppm | 49 ppm | 51 ppm | AVERAGE |
| Ormosil (ATS) | 0.968 | 0.984 | 0.968 | 0.946 | 0.967 |
| Ormosil (ATS)/Ag-0.05 | 0.786 | 0.821 | 0.921 | 0.908 | 0.859 |

Embodiment 6

Electron Paramagnetic Resonance Spectrometer Analysis

Electron Paramagnetic Resonance Spectrometer (EPR) is used to discuss the electron environment of Ag, wherein X-Band its microwave frequency is 9 GHz, and its temperature range is 4K-463K and 77K; German BRUKER, EMX-10.

Figure 6A:
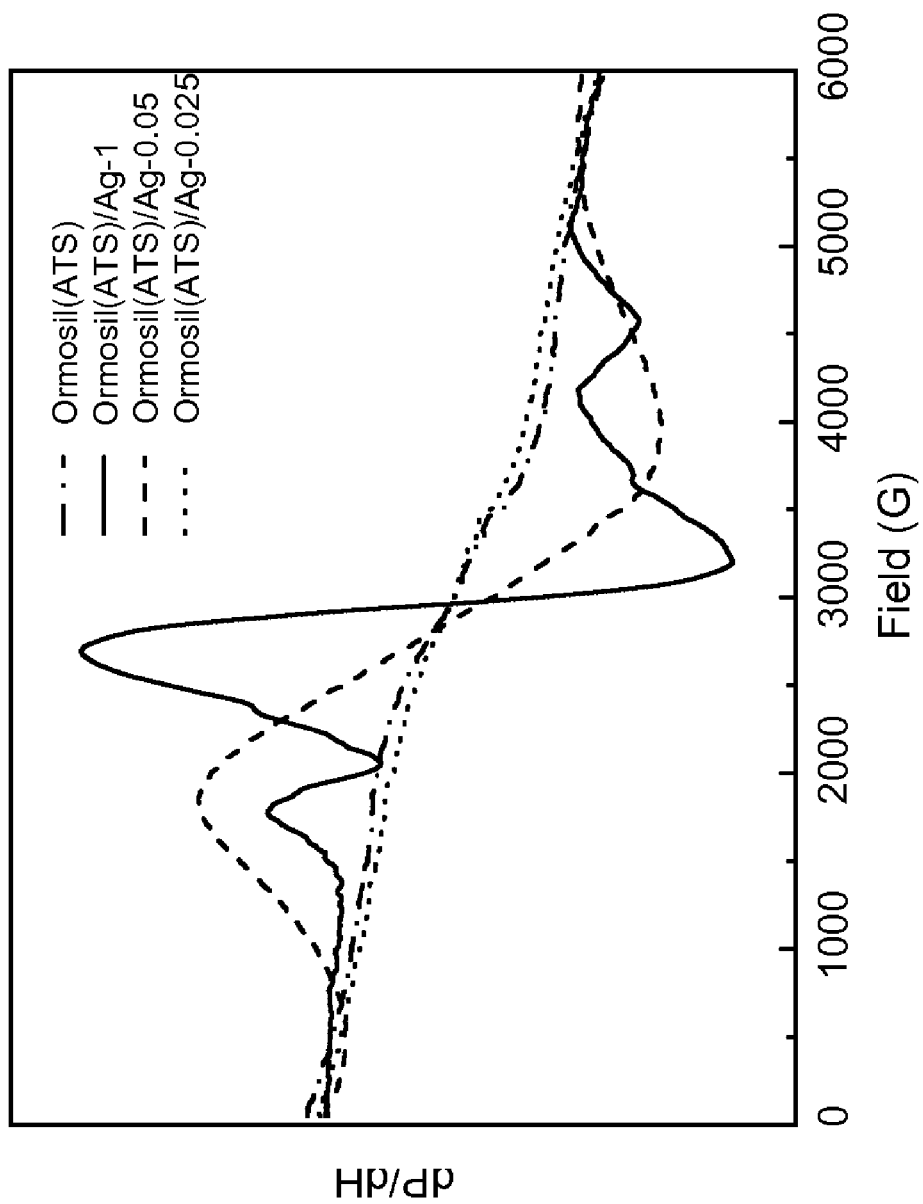
FIG. 6A is an EPR spectrum diagram illustrating Ormosil (ATS) and Ormosil(ATS)/Ag complexes with different silver content.
Figure 6B:
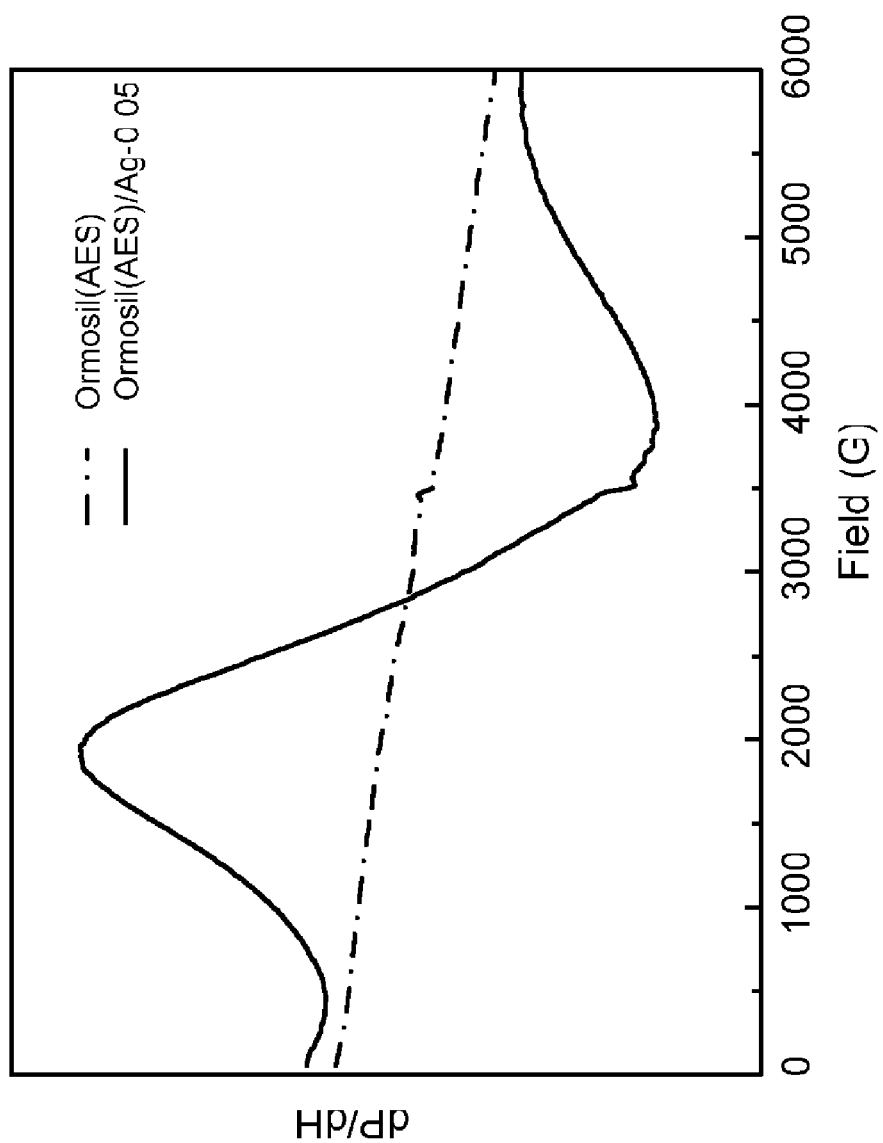
FIG. 6B is an EPR spectrum diagram illustrating Ormosil (AES) and Ormosil(AES)/Ag-0.05 complexes with different silver content.

Please refer to FIG. 6A and FIG. 6B. FIG. 6A is an EPR spectrum diagram illustrating Ormosil(ATS) and Ormosil (ATS)/Ag complexes with different silver content. FIG. 6B is an EPR spectrum diagram illustrating Ormosil(AES) and Ormosil(AES)/Ag-0.05 complexes with different silver content. As shown in the figures, Ormosil(ATS) and Ormosil (AES) have no EPR absorption because they do not have free electron or unpaired electron, and the electron paramagnetic resonance spectrum absorption of Ag is generated when the metal silver is absorbed in Ormosil. Ormosil(ATS)/Ag-0.1 complex has two EPR absorption peaks which indicate that the Ag has two kinds of electron environments, one is the Ag reacted with the amino group of Ormosil, and the other is the Ag with free state. Both of Ormosil(ATS)/Ag-0.05 and Ormosil(AES)/Ag-0.05 have an EPR absorption peak which belongs to the characteristic absorption of the metal silver, and has wider wave peak because of the action with the amino group of Ormosil. Ormosil(ATS)/Ag-0.025 complex has no EPR absorption peak possibly because the content of the Ag is too low.

Embodiment 7

Scanning and Transmission Electron Microscope Analysis

In the embodiment, the Field Emission Scanning Electron Microscope (FE-SEM) is JEOL JEM-200CX, which is 10~500,000 times, and the Transmission Electron Microscope (TEM) is PHILIPS CM-200.

According to the observation of said instruments, Ormosil (ATS)'s surface is smooth, which is good for siloxane hydrolysis condensation degree. The surface of Ormosil (ATS)/Ag complex distributes nano-scale Ag grains evenly, whose average grain diameter is about 10-30 nm. In addition, the grains distributed on Ormosil are metal silver, which can be approved by X-ray spectrum analysis. Additionally, the content of the Ag grains reduces along with the proportion of AgNO₃ (as shown in Table 2) and there is no phenomenon of grain accumulation. It is proved that the Ormosil comprising amino group can absorb and disperse the Ag grains effectively.

stage is the decomposition of the silica $T^i$ meshed segment at the temperature of 300~500° C. The cracking of the fourth stage is the decomposition of the silica $Q^i$ meshed segment at the temperature higher than 500° C. The thermal property of the Ormosil(ATS)/Ag complex is similar to Ormosil(ATS).

TABLE 2

| | Weight % | | | | Atom % | | | |
|---|---|---|---|---|---|---|---|---|
| Element | Ormosil (ATS) | ATS/Ag 0.1 | ATS/Ag 0.05 | ATS/Ag 0.025 | Ormosil (ATS) | ATS/Ag 0.1 | ATS/Ag 0.05 | ATS/Ag 0.025 |
| C | 44.00 | 40.35 | 37.49 | 30.28 | 55.91 | 53.90 | 48.584 | 40.05 |
| O | 33.27 | 31.72 | 40.89 | 47.99 | 31.74 | 31.81 | 39.78 | 47.66 |
| Si | 22.73 | 24.00 | 20.77 | 21.71 | 12.35 | 13.71 | 11.51 | 12.27 |
| Ag | | 3.93 | 0.85 | 0.02 | | 0.58 | 0.12 | 0.01 |
| Total content | 100 | 100 | 100 | 100 | 100 | 100 | 100 | 100 |

In addition, it is found that the content of the Ag grain distributed on the surface of Ormosil(ATS)/Ag-0.05 is higher than the one of Ormosil(AES)/Ag-0.05 in the analysis. It means the Ormosil(ATS) comprising long-chain amino group absorbs more Ag (as shown in Table 3), and it proves indirectly that the metal silver is indeed absorbed at the position of the amino group. Hence, the more the amino group (ATS) is contained, the more the content of the absorbed Ag has. In addition, according to said instruments, it is found that the dispersion of the Ag and the covering ability of the Ormosil are perfect, and no massive accumulation of the Ag occurred. In addition, it can be proved the existence of multi-crystal and single-crystal metal silver by using the electron diffraction pattern.

When few silver atoms (Ag-0.025) is added into the complex, the thermal property of the complex enhances obviously (the cracking rate slows down) and the char yield also increases. However, when the silver atoms increases (Ag-0.05 and Ag-0.1), the thermal property also increases, but the thermal cracking speeds up at the temperature higher than 550-600° C. It is because that few silver atoms increase the compactness of the Ormosil's structure and enhance its thermostability thereof. However, the silver atoms have good heat conductivity at high temperature. That's why the thermal cracking is speeded up when the silver content is increased.

Figure 7A:
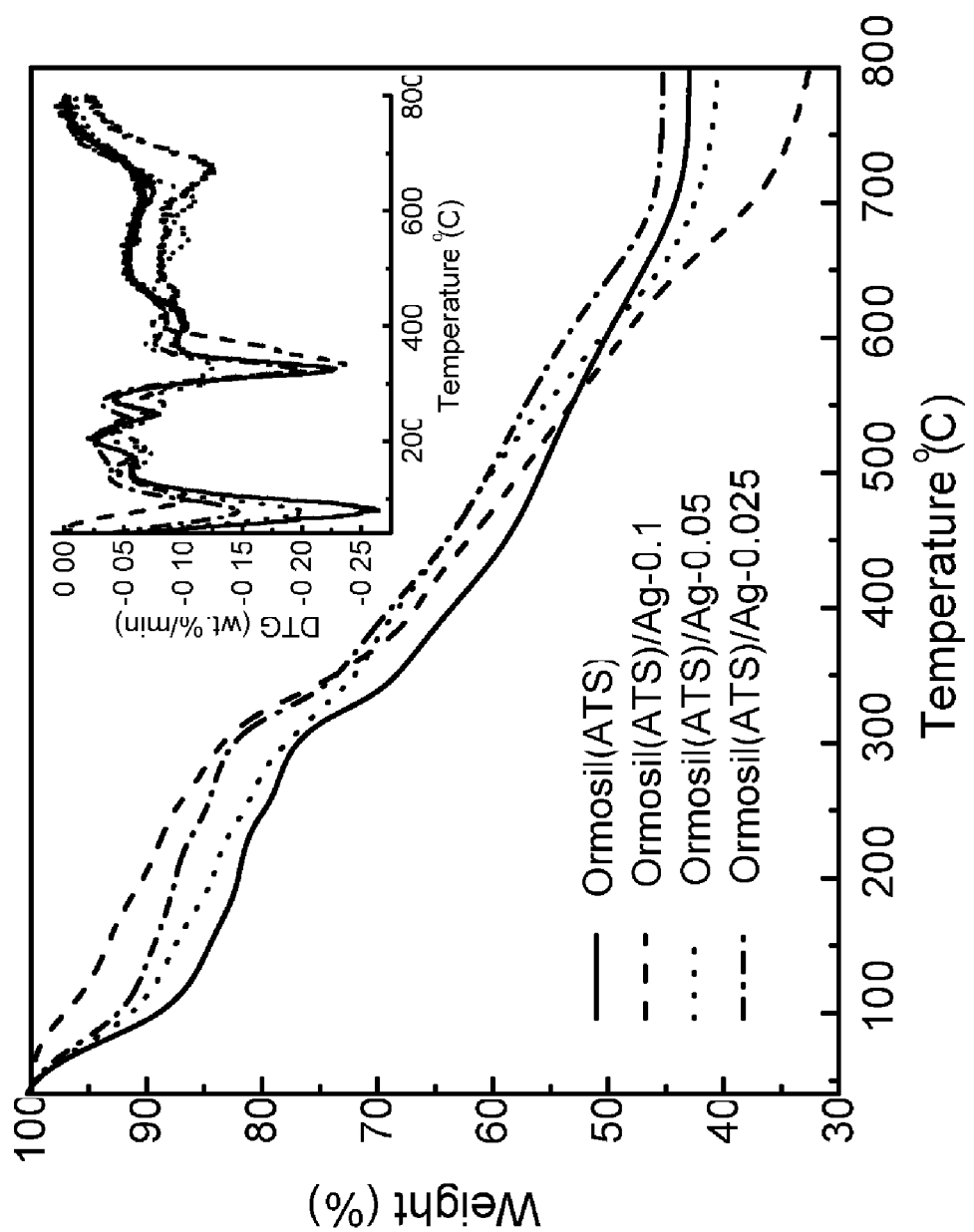
FIG. 7A is a TGA and DTA diagram illustrating Ormosil (ATS) and Ormosil(ATS)/Ag complexes in argon.
Figure 7B:
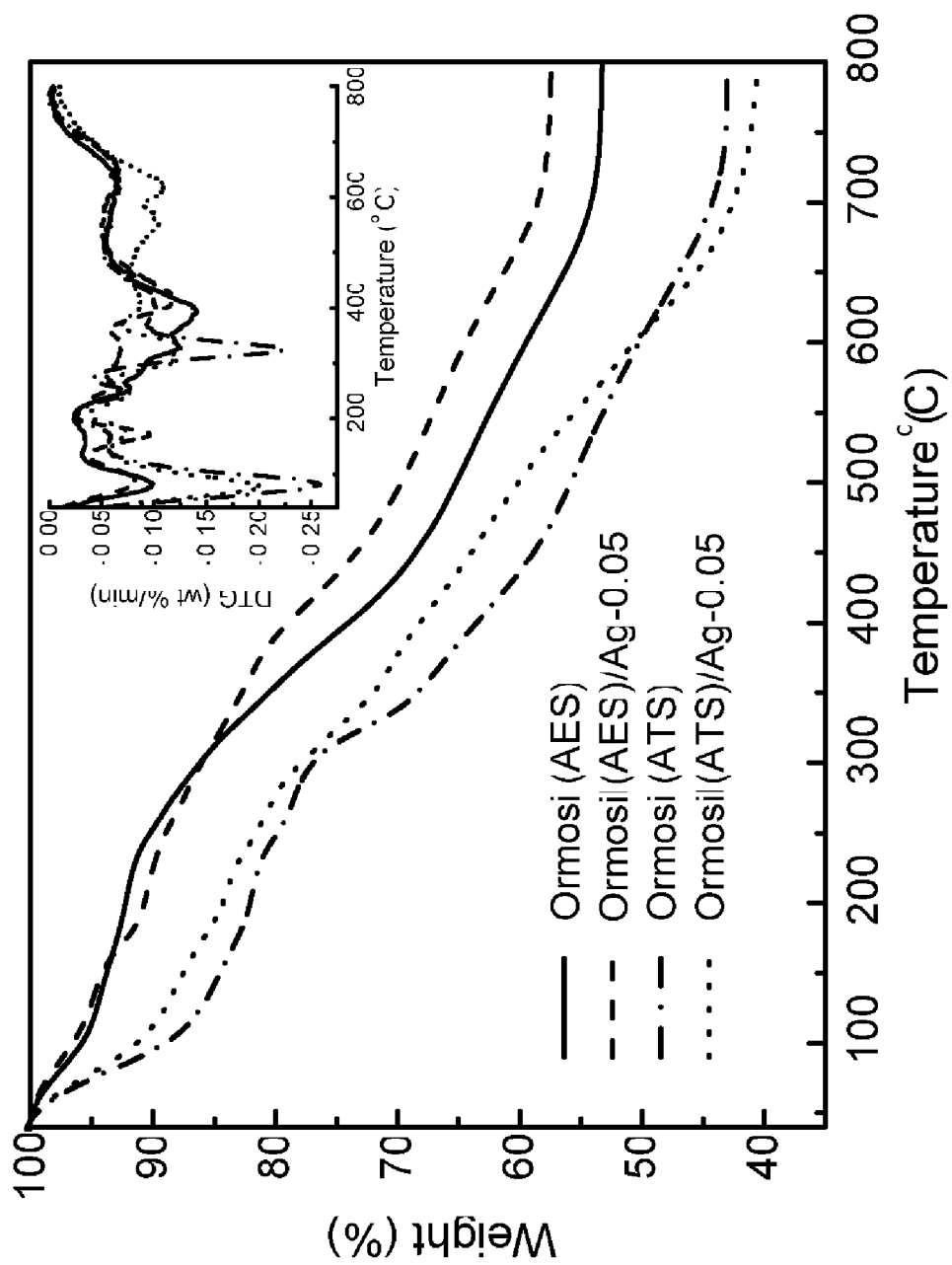
FIG. 7B is a TGA and DTA diagram illustrating Ormosil (AES), Ormosil(AES)/Ag-0.05, Ormosil(ATS) and Ormosil (ATS)/Ag-0.05 complexes in argon.

FIG. 7B is a TGA and DTA diagram illustrating Ormosil (AES), Ormosil(AES)/Ag-0.05, Ormosil(ATS) and Ormosil (ATS)/Ag-0.05 complexes in argon. It can be observed in the

TABLE 3

| | Weight % | | | | Atom % | | | |
|---|---|---|---|---|---|---|---|---|
| Element | Ormosil (AES) | AES/Ag 0.05 | Ormosil (ATS) | ATS/Ag 0.05 | Ormosil (AES) | AES/Ag 0.05 | Ormosil (ATS) | ATS/Ag 0.05 |
| C | 31.87 | 37.06 | 44.00 | 37.49 | 43.78 | 47.54 | 55.91 | 48.584 |
| O | 36.50 | 43.37 | 33.27 | 40.89 | 37.64 | 41.77 | 31.74 | 39.78 |
| Si | 31.63 | 19.47 | 22.73 | 20.77 | 18.58 | 10.68 | 12.35 | 11.51 |
| Ag | | 0.10 | | 0.85 | | 0.01 | | 0.12 |
| Total content | 100 | 100 | 100 | 100 | 100 | 100 | 100 | 100 |

Embodiment 8

Thermostability Analysis

In the embodiment, PerkinElmer Thermal Analysis TGA-7 is used here for further analysis. Thermal gravimetric analyzer (TGA): Du Pont instruments 951 thermgravimetric analyzer is used for thermal gravimetric loss and cracking dynamics analysis, wherein its temperature range is from 25 to 800° C., argon flow is 100 mL/min and heating rate is 20° C./min.

FIG. 7A is a TGA and DTA diagram illustrating Ormosil (ATS) and Ormosil(ATS)/Ag complexes in argon. It can be found that there are four stages of cracking for the Ormosil (ATS): the first stage is at the temperature of 50~200° C. and should be the dehydration of the complex absorbing water. The weight loss of the second stage is at the temperature of 200~300° C. and may attribute to the cracking of the fatty amine segment of the aminosilane. The cracking of the third figure that the Ormosil(AES) having short-chain amino group has better thermostability than the Ormosil(ATS) having long-chain amino group. It's because the Ormosil(AES) comprising short-chain amino group has more compact meshed structure and the thermostability also increases. In addition, the thermostability of the Ormosil(AES)/Ag-0.05 is better than the one of the Ormosil(AES), whose cracking rate slows down and char yield increases. But the Ormosil(ATS)/Ag-0.05 comprising long-chain amino group has an opposite result. It's because that the Ormosil(ATS)/Ag-0.05 comprising long-chain amino group absorbs more silver atoms under equal AgNO₃ (0.05 wt %) content, wherein the thermostability of the Ormosil(ATS)/Ag-0.05 is worse due to the heat conductivity of the silver atoms. The phenomenon shows that the meshed structure of the Ormosil(AES) is more compact after the silver atoms are added. Suitable content of the silver atoms could increase the thermostability of the Ormosil. The char yield percentage of the complex at the temperature 800° C. is: Ormosil(AES)/Ag-0.05>Ormosil(AES)>Ormosil (ATS)>Ormosil(ATS)/Ag-0.05.

Embodiment 9

Corrosion-Resistant Analysis

In the embodiment, a salt-spray tester (ELITE, ST-BZ-7) is used carry on a salt-spray test, wherein the salt-water concentration is 5 wt. %, the test area is 5×5 cm$^2$, the test environment temperature is 35° C. and the pressure is 1 atmosphere. The test time is 168 hours and a metallographic microscope (300×) is used to observe and record whether the specimen has rust or not every 24 hours.

A silane coupling agent is helpful to promote the corrosion-resistant of aluminum alloy in the research. The possible reason is that the non-hydrolytic functional group of the coupling agent is easier to promote the hydrolytic functional group and the hydroxyl group of the metal's surface to carry on the dehydration, to form the chemical bonding, and to generate the shielding chlorine ion effect. In the experiment, anti-bacterial nano-scale silver grains are tried to add in the coating, so that to increase the compactness of the coating as well as increase the anti-bacterial or corrosion-resistant effects on the coating or the film. An AC impedance electrochemistry analyzer is used to test the electrochemical characteristic of the complex material, and the experimental data shows that the corrosion potential of the aluminum alloy migrates toward positive potential after processing, wherein the reason is that the Ormosil comprises high conductivity Ag which makes the potential migrates towards positive potential. However, the corrosion current $I_{corr}$ of the aluminum alloy drops after processing through the Ormosil and Ormosil/Ag, which means the corrosion-resistant increases. The corrosion current $I_{corr}$ of the Ormosil/Ag is still higher than the one of the Ormosil, which is mainly because the silver atoms have good conductivity. Hence, the content of the silver atoms is considered in the application of the Ormosil/Ag on the corrosion-resistant of the aluminum alloy.

In the salt-spray test, the metallographic microscope is used to observe the corrosion phenomenon of the aluminum alloy's surface. After three days of the salt-spray test pass, 2024-T3 blank aluminum alloy piece has partial corrosion, the aluminum alloy pieces coated with the Ormosil(AES) and the Ormosil(ATS) have no corrosion, while the aluminum alloy pieces coated with the Ormosil(AES)/Ag and the Ormosil(ATS)/Ag have small partial of corrosion. After seven days of the salt-spray test pass, the blank aluminum alloy piece has a large-range of corrosion, he aluminum alloy pieces coated with the Ormosil(AES) and the Ormosil(ATS) have small partial of corrosion, while the aluminum alloy pieces coated with the Ormosil(AES)/Ag and the Ormosil(ATS)/Ag also have large-range of corrosion. The result of the salt-spray experiment shows that the Ormosil(AES) and the Ormosil (ATS) have the corrosion-resistant effect for 168 hours, and their corrosion-resistant are better than the one of the Ormosil (AES)/Ag and the Ormosil(ATS)/Ag. This result is identical with the one of the electrochemical method testing the corrosion current. It is mainly because of the conductivity of the silver atoms reducing the corrosion-resistant of the Ormosil (AES)/Ag and the Ormosil(ATS)/Ag.

Embodiment 10

Anti-Bacterial Analysis

In the embodiment, S. aureus, B. subtilis, P. aeruginosa and E. coli are cultures used for the research of the anti-bacterial susceptibility test and also to be the reference cultures of the anti-bacterial test, which are provided by Hsin-Chu Food Industry Development Research Institute. All of the cultures are stored in Nutrient broth, Difco Laboratories, USA and 15% glycerine which are cultivated in cold-storage −70° C. The solution of the anti-bacterial test is formulated by Mueller Hinton medium (Difco) before using, while the cultures are nurtured overnight by using nutrient agar in oxygen-containing chemostat at 37° C.

The qualitative testing process is as the following list: firstly, paper ingots (6 mm) are sterilized (120° C.) and drops into 30 μL sterilized water one by one. Then, 10 mg Ormosil and different proportions of Ormosil/Ag powder are moistened respectively. After that, the paper ingots moistening the samples are put in the Mueller Hinton agar (MHA) plates of the complete inoculation cultures. Finally, the plates are put in 37° C. thermostatic chemostat to nurture 24 hours and then test their bacteriostatic diameter. The quantitative test process is as the following list: firstly, suitable quantity of Ormosil or Ormosil/Ag powder are put in 5 mL Mueller Hinton broth (MHB) nurturing tubes. Then, the testing organism of each milliliter 107 bacteria ($10^7$ cfu/ml) is inoculated. After that, the nurturing tubes are nurtured for 18 hours in the oxygen-containing thermostatic at 37° C. to observe the growing number of the bacteria.

Each 10 mg of the Ormosil and the Ormosil/Ag complexes are listed as the following Table 4 to resist the related biological activity (bacteriostasis circle) of S. aureus, B. subtilis, P. aeruginosa and E. coli. After 24 hours, the bacteriostasis circle range of the Ormosil and the Ormosil/Ag complexes resisting said cultures are respectively 16.27-26.39 mm and 8.62-10.86 mm. It is obvious that the Ormosil(ATS) has better anti-bacterial effect. It's mainly because the Ormosil(ATS) comprises more amino groups. In addition, the effect of resisting said microbiota for the Ormosil(ATS)/Ag and the Ormosil(AES)/Ag complexes is better than the one of the Ormosil(ATS) and Ormosil(AES).

TABLE 4

| | | Ormosil(ATS)/Ag | | | Ormosil(AES)/Ag | |
|---|---|---|---|---|---|---|
| Strain | Blan | ATS | Ag-0.1 | Ag-0.05 | Ag-0.025 | AES | Ag-0.05 |
| S. aureus | 0 | 16.27 | 17.93 | 16.90 | 21.96 | 10.86 | 11.11 |
| B. subtilis | 0 | 26.39 | 30.09 | 30.89 | 27.68 | 8.62 | 15.03 |
| P. aeruginosa | 0 | 20.68 | 26.00 | 24.03 | 20.36 | 8.62 | 8.62 |

In addition, the experimental result also shows that along with the content of the complex increases (0→50 mg), the number of S. aureus is reduced obviously (340000→400). Other cultures also have the same result. It means that the Ormosil(ATS)/Ag and the Ormosil(AES)/Ag complexes have wonderful anti-bacterial effect on S. aureus, B. subtilis, P. aeruginosa and E. Coli, wherein the Ormosil(ATS)/Ag complex is better.

To sum up, the method of the invention has synthesized successfully the anti-bacterial compositions of the Ormosil (ATS)/Ag and the Ormosil(AES)/Ag with different silver content. It is proved that the nano-scale metal atoms can be well dispersed in the meshed structure of the Ormosil without the phenomenon of congregation according to the result of the spectrum analysis. The Ormosil(ATS) comprising long-chain amino group can absorb more silver atoms and hence has better dispersion effect. In addition, the thermostability of the Ormosil/Ag comprising suitable quantity of silver atoms is better than the one of the Ormosil. Moreover, the Ormosil/Ag and the Ormosil complexes have good anti-bacterial effect on

*S. aureus, B. subtilis, P. aeruginosa* and *E. coli*, wherein the Ormosil(ATS)/Ag complex is better.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of manufacturing an anti-bacterial composition, said method comprising the steps of:
    (a) mixing tetraethyl orthosilicate with aminosilane, stirring the mixture in nitrogen to form an organic siloxane material comprising an amino group, and the organic siloxane material having a meshed structure;
    (b) dissolving silver salts in ammonium hydroxide and adding the dissolved silver salts into the organic siloxane material to dissociate silver ions from the silver salts; and
    (c) adding hydrazine into the mixture of step (b), stirring the mixture in nitrogen to reduce the silver ions to form silver atoms, so that the silver atoms are well dispersed in the meshed structure of the organic siloxane material to obtain the anti-bacterial composition.

2. The method of claim 1, wherein the molar concentration ratio of the tetraethyl orthosilicate and the aminosilane is 1:1.

3. The method of claim 1, wherein the aminosilane is 3-(2-aminoethylaminopropyl)trimethoxysilane (AES) or N-[3-(trimethoxysilyl)propyl]diethylenetriamine (ATS).

4. The method of claim 1, wherein the silver salts are silver nitrate.

* * * * *